United States Patent [19]

Telschow

[11] Patent Number: 4,559,405
[45] Date of Patent: Dec. 17, 1985

[54] PROCESS FOR PREPARING SUBSTITUTED PHTHALIC ANHYDRIDES

[75] Inventor: Jeffrey E. Telschow, Tarrytown, N.Y.

[73] Assignee: Stauffer Chemical Company, Westport, Conn.

[21] Appl. No.: 600,248

[22] Filed: Apr. 16, 1984

[51] Int. Cl.$^4$ ............................................. C07D 307/89
[52] U.S. Cl. .................................... 549/240; 549/243; 549/245; 549/246
[58] Field of Search ................ 549/240, 243, 245, 246

[56] References Cited

U.S. PATENT DOCUMENTS 2,097,854 11/1937 Dilthey ................................. 549/240
2,264,429 12/1941 Bergmann ........................ 549/240 X
2,391,226 12/1945 Clifford et al. ...................... 549/240

OTHER PUBLICATIONS

Craig, JACS, vol. 72, (1950), pp. 3732 and 3733.
Newman et al., JACS, vol. 63, (1941), pp. 1542–1544.
Izv. Akad. Nauk SSSR, Ser Khim, vol. 6, (1973), p. 1315.

Primary Examiner—Richard L. Raymond
Attorney, Agent, or Firm—Hensley M. Flash

[57] ABSTRACT

A process for preparing substituted phthalic anhydrides, e.g. 4-methylphthalic anhydride, in which the Diels-Alder addition product of a conjugated diene, e.g. isoprene, and maleic anhydride is reacted with bromine in the presence of an acid acceptor. Typical acid acceptors include dimethylformamide and pyridine.

8 Claims, No Drawings

PROCESS FOR PREPARING SUBSTITUTED PHTHALIC ANHYDRIDES

BACKGROUND OF THE INVENTION

1. Field of the Invention

This invention relates to a process for preparing substituted phthalic anhydrides. More particularly, it relates to a process for preparing 4-methylphthalic anhydride.

2. Related Art

Phthalic anhydrides are valuable raw materials for making various useful products. These anhydrides are useful as intermediates in the chemical synthesis of herbicides and particularly in the synthesis of certain herbicides used to protect cereal crops. Other uses for these raw materials include polycyclic dyes, alkyd and epoxy resins, polyesters and plasticizers.

Various processes are known for preparing substituted phthalic anhydrides. In two such processes 4-methyl-1,2,3,6-tetrahydrophthalic anhydride is dehydrogenated either by sulfur or by bromine in acetic acid. Yields of 4-methylphthalic anhydride of 59%–87% are claimed for the former method, while the latter gives only a 16% yield [see IZV. Akad Nauk SSSR, Ser Khim, 6, 1315(1973) English trans. Pg. 1271 and D. Craig, Journal of Am. Chem. Soc., Vol. 72, Pg. 3732 (1950)].

U.S. Pat. No. 2,391,226 (Clifford et al., Dec. 18, 1945) discloses addition products of chlormaleic anhydride and dichlormaleic anhydride prepared by the Diels-Alder reaction and the dehydrochlorination of these products in the presence of a catalyst, such as a secondary or tertiary amine. However, the sixcarbon ring is usually only partially dehydrogenated yielding a substituted dihydrophthalic anhydride.

U.S. Pat. No. 2,264,429 (Bergman, Dec. 2, 1941) discloses a process for preparing substituted phthalic anhydride in a single reaction. This reaction involves the combination of the condensation reaction between a diene and maleic anhydride and the dehydrogenation reaction. This combination is achieved by carrying out the condensation reaction in nitrobenzene or another nitrated aromatic substance, which not only acts as a diluent, but also as a dehydrogenating agent by reducing itself and giving the corresponding amine. This patent discloses o-nitrotoluene as another example of a nitrated aromatic substance useful in the disclosed process.

SUMMARY OF THE INVENTION

A process for preparing substituted phthalic anhydrides in good yields would be advantageous because of the various useful products that are prepared from these anhydrides. It is an object of the present invention to provide a unique, cost effective process for the preparation of substituted phthalic anhydrides. Other objects and advantages of the present invention are shown throughout the specification.

In accordance with the present invention, it has now been discovered that substituted phthalic anhydrides can be prepared by a process which comprises reacting the Diels-Alder addition product of a conjugated diene and maleic anhydride with bromine in the presence of an acid acceptor.

DETAILED DESCRIPTION OF THE INVENTION

The present invention comprises a process for preparing substituted phthalic anhydrides by reacting the Diels-Alder addition product of a conjugated diene and maleic anhydride with bromine in the presence of an acid acceptor.

The substituted phthalic anhydrides of this invention can include a substituent or the lack of a substituent at each of the four available sites on the benzene ring, i.e. the 3,4,5 and 6 carbon positions. These substituents can be selected from the group consisting of $C_1$ to $C_{10}$ alkyl, $C_6$ to $C_{14}$ aryl and $C_1$ to $C_{16}$ aralkyl and wherein the alkyl, aryl and aralkyl are optionally substituted with halogens, nitro groups, cyano groups and carboxylic groups.

The process can use the Diels-Alder addition product as a starting material or can comprise a first step of actually preparing this addition product. The Diels-Alder addition product can be derived from other than the Diels-Alder reaction. In addition, the double bond isomers of the Diels-Alder addition product can be used in the process of this invention.

The Diels-Alder addition products of this invention are formed by reacting maleic anhydride with a conjugated diene. The conjugated diene can include butadiene, 2,3-dimethylbutadiene, other substituted butadienes and preferably isoprene.

The addition product can be prepared by reacting the maleic anhydride with the conjugated diene in a nitrogen atmosphere. The maleic anhydride is usually heated until it melts, then the conjugated diene is added slowly under the surface of the melt. When the addition of the diene is completed, the reactants can then be heated up to a reaction temperature of from about 55° C. up to about 120° C. with temperatures in the upper end of the range from about 100° C. up to about 120° C. being preferred. The reactants are kept within the reaction temperature range until the reaction is completed, usually for about 1 hour. The reaction can be exothermic, therefore external cooling can be required to maintain the reactants within the reaction temperature range.

After the reaction to form the addition product is completed, excess diene can be stripped from the reaction zone under vacuum at a pressure which minimizes sublimation of the addition product and distillation of the solvent.

The reaction used to prepare the addition product can take place in the presence or absence of an appropriate solvent. Such a solvent can be dimethylformamide (DMF). When DMF is used, a solution of the addition product in DMF results and no solids are formed during the reaction. The bromination step can then be carried out directly upon this DMF/addition product solution after excess diene is stripped from the reaction zone. The DMF in this instance would act both as a solvent and as an acid acceptor reagent.

The stoichiometry of this Diels-Alder addition reaction usually involves one mole of the maleic anhydride reacting with one mole of the conjugated diene to produce one mole of the addition product, therefore it is economically desirable to react equimolar quantities of the reactants. However, a fractional molar excess of the diene is usually used to ensure that all the maleic anhydride is consumed in the reaction.

When the Diels-Alder addition product is used as a starting material, the following procedure can be used in accordance with this invention. The addition product is made up into a solution with a suitable solvent and the acid acceptor reagent is added to this solution. Some examples of suitable solvents are chlorobenzene and DMF. When DMF is used as the solvent, a sufficient quantity is used so that DMF can also participate in the reaction as the acid acceptor reagent.

Bromine can then be added slowly to the reactor. After the bromine addition begins, a hydrogen bromide/acid acceptor adduct will begin to form and may or may not precipitate from solution. The bromine addition can be mildly to moderately exothermic. During the bromine addition, the temperature in the reaction zone is maintained at from about 35° C. up to about 150° C. When a solvent is used in the reaction a temperature range of from about 35° C. up to the boiling point of the solvent is preferred.

After the bromine addition is completed, the temperature within the reaction zone can be slowly increased to a range from about 70° C. up to about 180° C. to ensure completion of the reaction.

After the reaction is completed, a crude solution remains within the reactor. This crude solution can then be cooled to temperatures from about 0° C. up to about 60° C. and then water can be added. Two separate layers, an aqueous and an organic layer result, which can be separated. When DMF is used as both the solvent and the acid acceptor reagent, chloroform can be used to extract the substituted phthalic anhydride. Chloroform is then added prior to the addition of water and the aqueous layer can be washed with chloroform after the separation of layers. Chlorobenzene can also be used as an extraction and washing agent. The organic layers can then be combined, concentrated and distilled to form the desired end product, substituted phthalic anhydride.

The acid acceptors that can be used in this process are varied, however pyridine and dimethylformamide are preferred, with DMF being most preferred. DMF is less costly than pyridine and no solids are formed during the reaction when DMF is used as both the solvent and the acid acceptor reagent.

The stoichiometry of the dehydrogenation reaction usually involves one mole of the addition product reacting with two moles of bromine and four moles of the acid acceptor to produce one mole of the substituted phthalic anhydride. It is therefore economically desirable to react quantities of the reagents that are proportionate to this stoichiometry.

In a preferred embodiment of this invention, 4-methylphthalic anhydride, (4-MPA), is prepared. This process comprises reacting 4-methyl-1,2,3,6-tetrahydrophthalic anhydride, (4-MTPA), with bromine in the presence of an acid acceptor. The acid acceptors used can be dimethylformamide, (DMF), or pyridine with DMF being most preferred. This process can be carried out in the presence of an appropriate solvent such as chlorobenzene or even an excess of DMF. The 4-MPA resulting from this process can be distilled after an aqueous work-up/solvent extraction step.

In another preferred embodiment 4-MPA can be prepared by a process which comprises a first step of reacting isoprene and maleic anhydride to form the Diels-Alder addition product, 4-MTPA, then proceeding to react the 4-MTPA with bromine in the presence of an acid acceptor as described above.

The following Examples describe various embodiments of the invention. Other embodiments will be apparent to the skilled in the art from a consideration of this specification or practice of the invention disclosed herein. It is intended that the specifications and Examples be considered as exemplary only, with the true scope and spirit of the invention being indicated by the claims which follow the Examples.

EXAMPLE 1

In a 1 liter 3-necked flask fitted with a dropping funnel, a mechanical stirrer, a pot thermometer and a condenser was placed 98.1 gms (1.0 mole) of maleic anhydride. The flask was heated in an oil bath until the maleic anhydride melted. Isoprene (69.5 gms, 1.02 moles) was then added dropwise to the flask below the surface of the maleic anhydride melt, using an extension tube of TEFLON fluorocarbon polymer attached to the dropping funnel, at such a rate as to minimize the reflux. The temperature of the reactants in the flask was controlled with intermittent cooling and kept between 55° C. and 100° C.

After the addition of the isoprene was completed, the reactor flask was heated to 120° C. and maintained at that temperature for 60 minutes to ensure complete reaction. Excess isoprene was then stripped from the reactor at 100 mm/90° C. for 20 minutes.

The faintly yellow, molten 4-methyl-1,2,3,6-tetrahydrophthalic anhydride (4-MTPA, mp 58°–63° C.) was formed in the reactor flask.

EXAMPLE 2

A 2 liter 3-necked flask was fitted with a heating mantle, a pot thermometer, a 250 ml dropping funnel, a mechanical stirrer and a condenser. The flask was charged with 98.1 gms (1.0 mole) of maleic anhydride and 400 mls of dimethylformamide (DMF), then the resulting solution was heated to 55° C. A total of 110 mls of isoprene (74.9 gms, 1.1 moles) was added dropwise to the flask while maintaining the temperature of the reactants within the flask between 55° C. to 90° C. by means of intermittent cooling in a cold water bath.

After the addition of isoprene was completed, the solution in the reactor flask was heated to the 90° C. to 100° C. range and maintained at that temperature for 60 minutes to ensure complete reaction. The solution was then cooled to 50° C. and then excess isoprene was stripped from the reactor at 50 mm Hg for 30 minutes.

After stripping, the remaining solution was returned to atmospheric pressure, the temperature was adjusted to 60° C., and bromine was added dropwise. The temperature of the solution began to increase with the bromine addition and was allowed to reach a temperature range of between 80° C. to 90° C. This temperature range was maintained throughout the 2 hours bromine addition by gentle cooling.

After the bromine addition was completed, the dark solution that resulted was heated to a temperature range of between 110° C. to 120° C. and maintained at that temperature for 1 hour. The solution was cooled to below 60° C., diluted with 400 mls of chloroform, and then further cooled to 20° C.

The stirred solution was treated with 400 mls of water and the aqueous phase was separated and extracted again with 400 mls of chloroform. The combined chloroform layers were washed with 600 mls of water and then stripped to a brown crystalline residue via a rotary evaporator.

The crude residue was vacuum distilled using a 3" Vigreaux column and a short, uncooled condenser to give 132.3 gms (82% yield based on maleic anhydride) of a yellow liquid, 4-MPA, which later solidified (bp 150° C.–160° C./10 mm, mp 75° C.–89° C.).

EXAMPLE 3

A solution of 16.6 gms (0.10 mole) of 4-MTPA in 60 mls of chlorobenzene and 32.7 mls (32 gms, 0.404 moles) of pyridine was prepared in a 3-necked flask. Bromine (10.3 mls, 32.1 gms, 0.202 moles) was added dropwise to this solution.

The temperature of the reactants began to increase with the bromine addition and was allowed to reach a temperature range of between 35° C. to 42° C. This temperature range was maintained until the bromine addition was completed, then the reactants were heated to 70° C. and maintained at this temperature for 30 minutes.

The reactants were cooled to 25° C. and 100 mls of water added to the flask. Two phases formed which were separated, and the aqueous phase was further extracted with two 25 mls portions of chlorobenzene. The combined organic fractions were concentrated under high vacuum to leave 14.1 gms (87% yield) of a yellow solid. This yellow solid was virtually pure 4-MPA when analyzed by g.c. and NMR.

What is claimed is:

1. A process for preparing 4-methylphthalic anhydride which comprises reacting 4-methyl-1,2,3,6-tetrahydrophthalic anhydride with bromine in the presence of an acid acceptor.

2. The process of claim 1 wherein the acid acceptor is dimethylformamide.

3. The process of claim 1 wherein the acid acceptor is pyridine.

4. The process of claim 3 wherein the reaction is carried out in the presence of chlorobenzene as a solvent.

5. A process for preparing 4-methylphthalic anhydride which comprises:
   (a) reacting isoprene and maleic anhydride to form 4-methyl-1,2,3,6-tetrahydrophthalic anhydride;
   (b) reacting the 4-methyl-1,2,3,6-tetrahydrophthalic anhydride with bromine in the presence of an acid acceptor.

6. The process of claim 5 wherein the acid acceptor is dimethylformamide.

7. The process of claim 5 wherein the acid acceptor is pyridine.

8. The process of claim 7 wherein step (b) is carried out in the presence of chlorobenzene as a solvent.

* * * * *